United States Patent [19]
Lampropoulos

[11] Patent Number: 5,507,720
[45] Date of Patent: Apr. 16, 1996

[54] SHIN AND ANKLE PROTECTOR

[76] Inventor: George Lampropoulos, 37 Valley Meadow Garden NW., Calgary, Alberta, Canada, T3B 5L8

[21] Appl. No.: 262,871

[22] Filed: Jun. 21, 1994

[51] Int. Cl.⁶ ............................................. A61F 5/00
[52] U.S. Cl. ..................... 602/27; 602/23; 602/65; 2/22
[58] Field of Search ..................... 2/22, 23, 24, 267, 2/268; 602/27, 60, 62, 63, 65, 27

[56] References Cited

U.S. PATENT DOCUMENTS

| | | | |
|---|---|---|---|
| 1,624,129 | 4/1927 | Barrett | 2/22 |
| 2,325,321 | 7/1943 | Hubner et al. | |
| 2,338,424 | 1/1944 | Giardini | |
| 2,733,443 | 2/1956 | Holder | |
| 3,383,708 | 5/1968 | Pappas | |
| 4,306,315 | 12/1981 | Castiglia | |
| 4,497,070 | 2/1985 | Cho | |
| 4,597,395 | 1/1986 | Barlow et al. | 602/26 |
| 4,621,648 | 11/1986 | Ivany | 602/26 |
| 4,628,945 | 12/1986 | Johnson, Jr. | |
| 4,674,157 | 6/1987 | Lintz | 2/22 X |
| 4,865,023 | 9/1989 | Craythorne et al. | 602/26 |
| 4,966,134 | 10/1990 | Brewer | 602/26 |
| 5,056,509 | 10/1991 | Swearington | 602/26 |
| 5,067,486 | 11/1991 | Hely | 602/26 |
| 5,199,941 | 4/1993 | Makinen | |
| 5,211,672 | 5/1993 | Andujar | 602/26 |
| 5,301,370 | 4/1994 | Henson | 2/24 |

Primary Examiner—Richard J. Apley
Assistant Examiner—Kim M. Lee
Attorney, Agent, or Firm—John D. Harris; Robert A. Wilkes

[57] ABSTRACT

The invention relates to a device for protecting a shin and ankle from blows and for supporting the ankle, allowing an athlete to participate in sports with an ankle injury. The device attachable to a shin, ankle and foot for protecting the shin and ankle from blows and for supporting the ankle against inversion and eversion, comprises a body comprising a shin protecting portion connected to an ankle supporting portion, the ankle supporting portion comprising two sides for positioning on the medial and lateral sides of the ankle respectively; means, such as straps, for securing the two sides of the ankle supporting portion of the body to the ankle; and a U-shaped support extending between the two sides of the ankle supporting portion of the body for passing under the foot. Preferably, the body comprises a hard outer shell and an inner pad. The shin protecting portion and the ankle supporting portion may be flexibly connected. The device avoids interference between conventional shin guards and ankle braces.

11 Claims, 6 Drawing Sheets

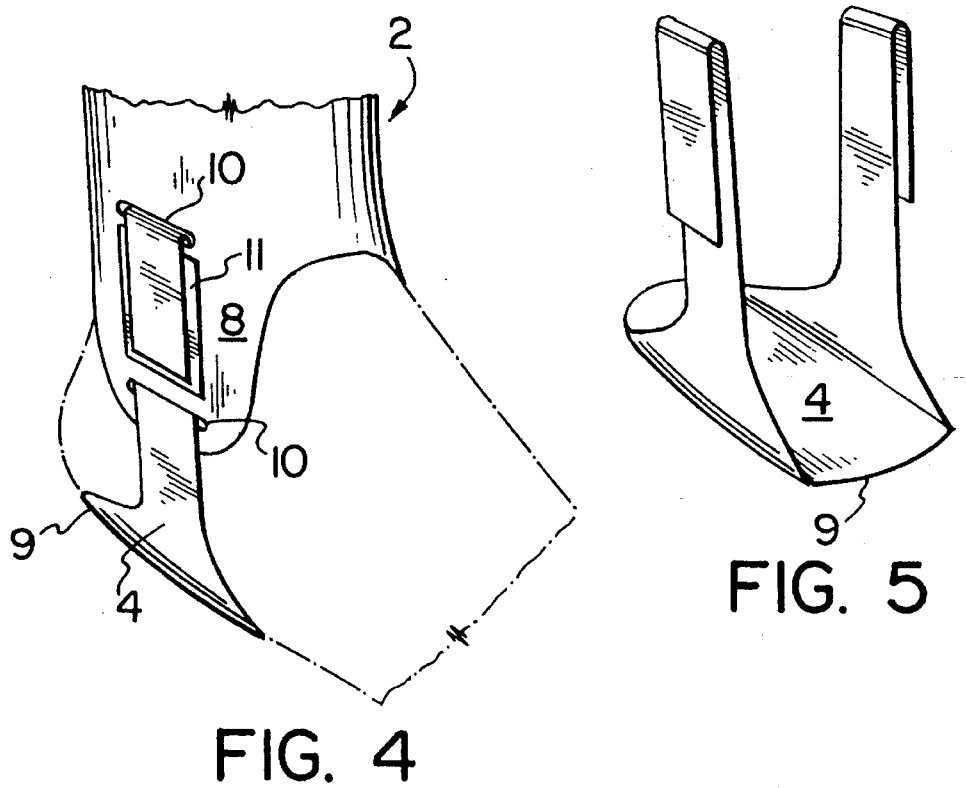
FIG. 4
FIG. 5
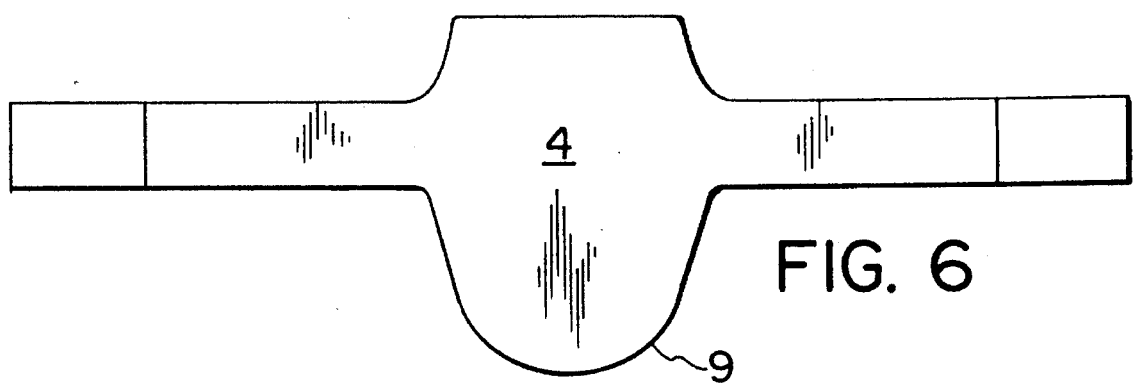
FIG. 6

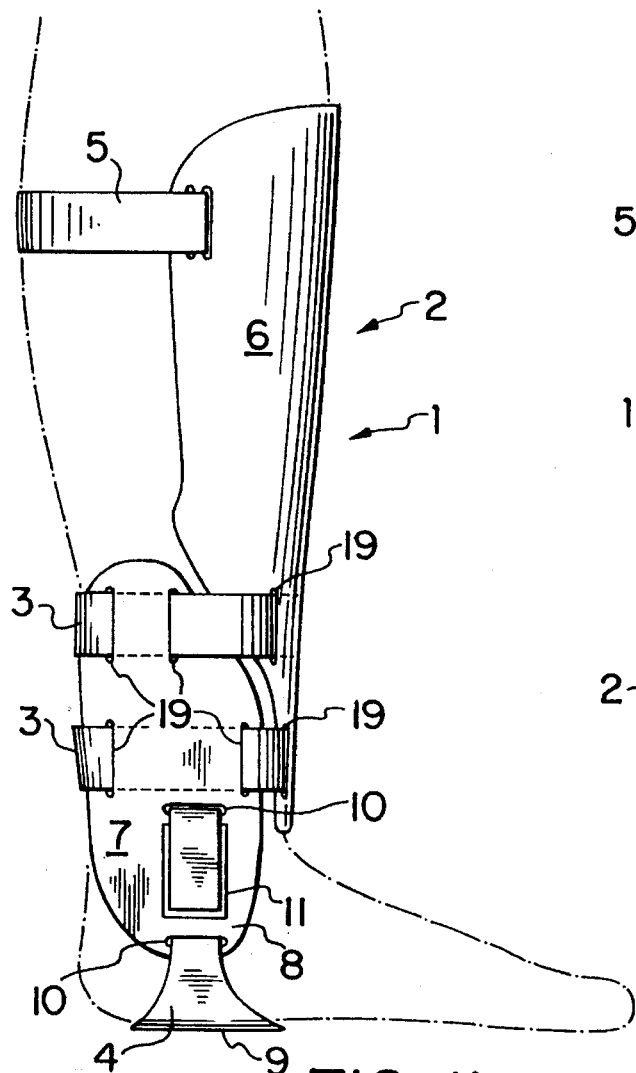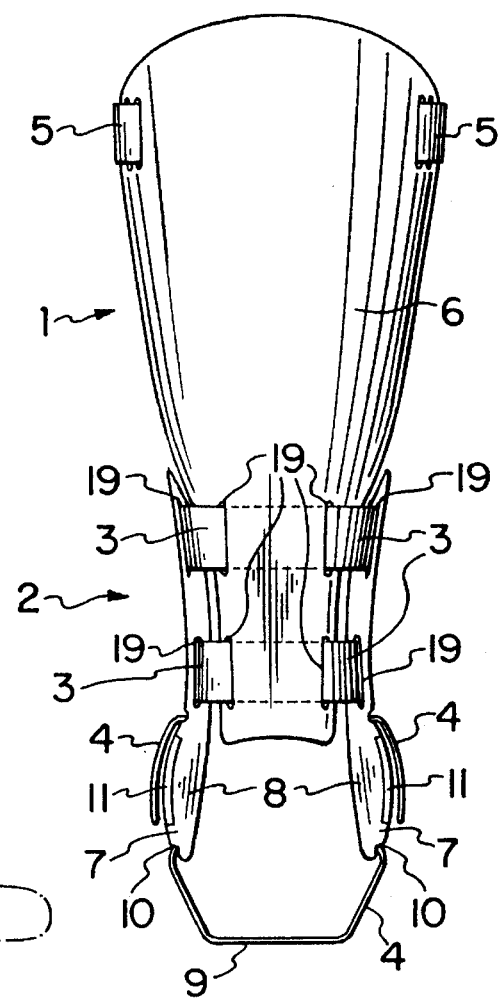

5,507,720

SHIN AND ANKLE PROTECTOR

FIELD OF INVENTION

This invention relates to a device for protecting a shin and ankle from blows and for supporting the ankle.

BACKGROUND OF THE INVENTION

It is common for players of various sports, such as soccer and field hockey, to wear shin guards to protect their shins from blows from various sources, such as cleats, balls and sticks. Game rules may, in fact, mandate the wearing of shin guards.

It is also common to participate in such sports with ankle injuries. Support must often be provided to injured ankles to allow them to heal and to prevent further injury. In such cases, it is desirable to support the ankle against inversion and eversion (that is, to restrict inversion and eversion of the ankle), while allowing substantially free dorsiflexion and plantarflexion of the ankle. A common solution is to apply tape or an elastic bandage to the ankle and foot, but such methods often provide inadequate support. Ankle braces generally offer superior support than bandages or tape and are easier to put on and take off than tape. Braces generally interfere with the wearing of shin guards however, and effective participation in sports which require the wearing of shin guards is thus precluded.

A soccer player, for example, may have an ankle injury requiring a brace which will preferably offer both support and protection from blows to the injured ankle. Game rules may require the wearing of shin guards (which is, in any case, highly desirable), and that shin guards and ankle braces be non-metallic and be worn under a sock. The shin guard and ankle brace must not interfere with one another, and the shape and weight of the ankle brace must be such that there is minimal interference with passing, kicking, trapping, dribbling, running, jumping, cutting, and the like.

SUMMARY OF THE INVENTION

The object of the invention is to provide a device for protecting the shin from blows and for supporting the ankle against inversion and eversion, while allowing the wearer of the device to play a sport. A secondary object of the invention is to protect the ankle from blows.

According to the invention, there is provided a device attachable to a shin, ankle and foot, for protecting the shin and ankle from blows and for supporting the ankle against inversion and eversion, the device comprising: a body comprising a shin protecting portion connected to an ankle supporting portion, the ankle supporting portion comprising two sides for positioning on the medial and lateral sides of the ankle respectively; means for securing the two sides of the ankle supporting portion of the body to the ankle; and a U-shaped support extending between the two sides of the ankle supporting portion of the body for passing under the foot.

The device disclosed and claimed herein has several advantages: it protects the shin from blows; it supports the ankle against inversion and eversion; it protects the ankle from blows; it allows dorsiflexion and plantarflexion of the ankle; it avoids interference between conventional shin guards and ankle braces; it is lighter than conventional shin guard, ankle brace combinations; it may be worn under a sock or other article of clothing; it is relatively convenient to put on and take off.

BRIEF DESCRIPTION OF THE DRAWINGS

The embodiments of the invention will now be described with reference to the accompanying drawings, in which:

FIG. 4 is a perspective view of part of the first embodiment of the invention;

FIG. 5 is a perspective view of the support strap of the first embodiment of the invention;

FIG. 6 is a top plan view of the support strap of the first embodiment of the invention;

FIG. 11 is a side elevation view of a fourth embodiment of the invention;

FIG. 12 is a front elevation view of the fourth embodiment of the invention.

Similar reference numerals are used in the various figures to denote similar components.

DETAILED DESCRIPTION OF THE INVENTION

Figure 1:
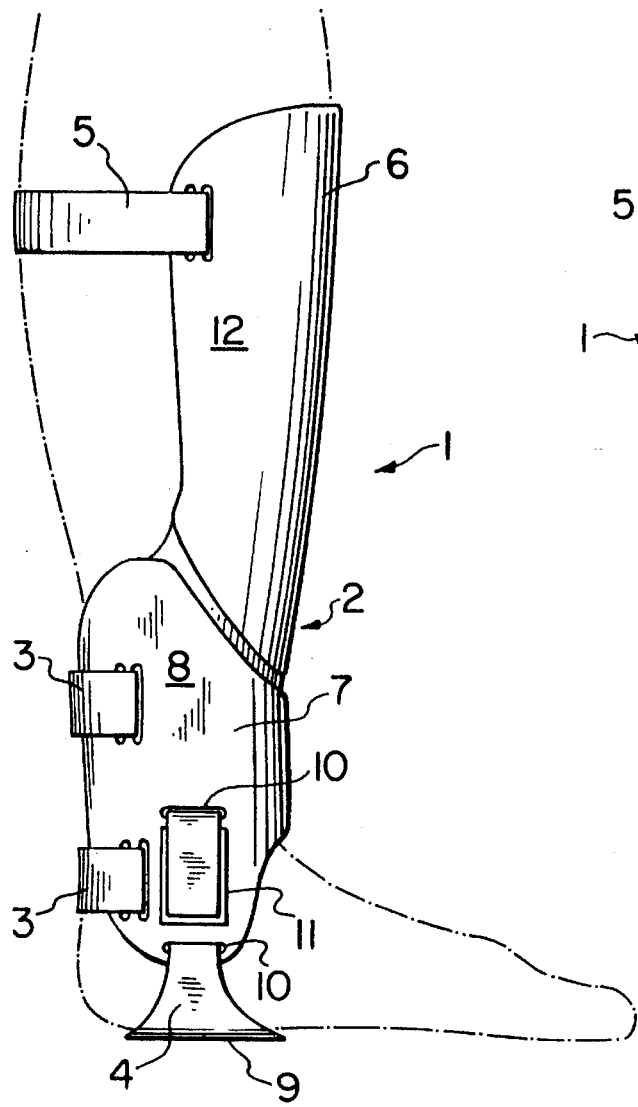
FIG. 1 is a side elevation view of a first embodiment of the invention.
Figure 2:
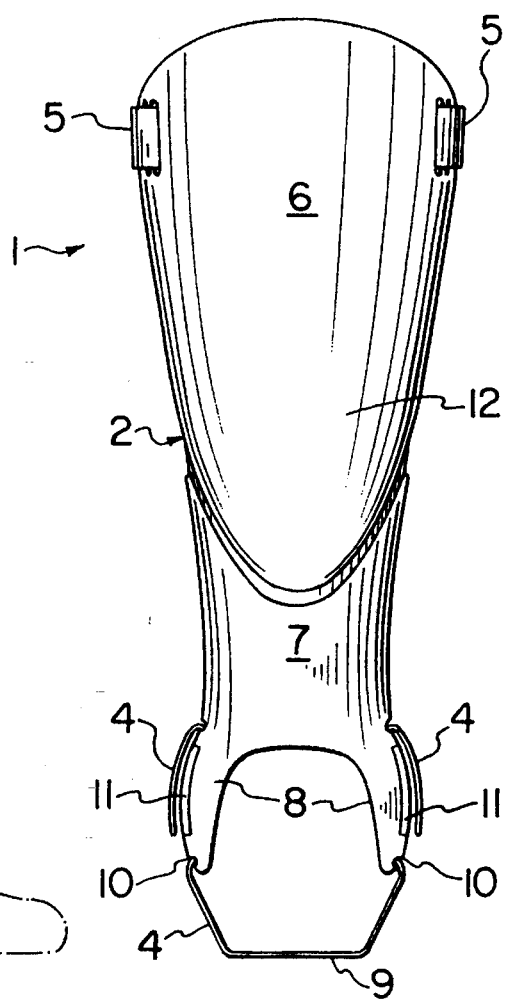
FIG. 2 is a front elevation view of the first embodiment of the invention.
Figure 3:
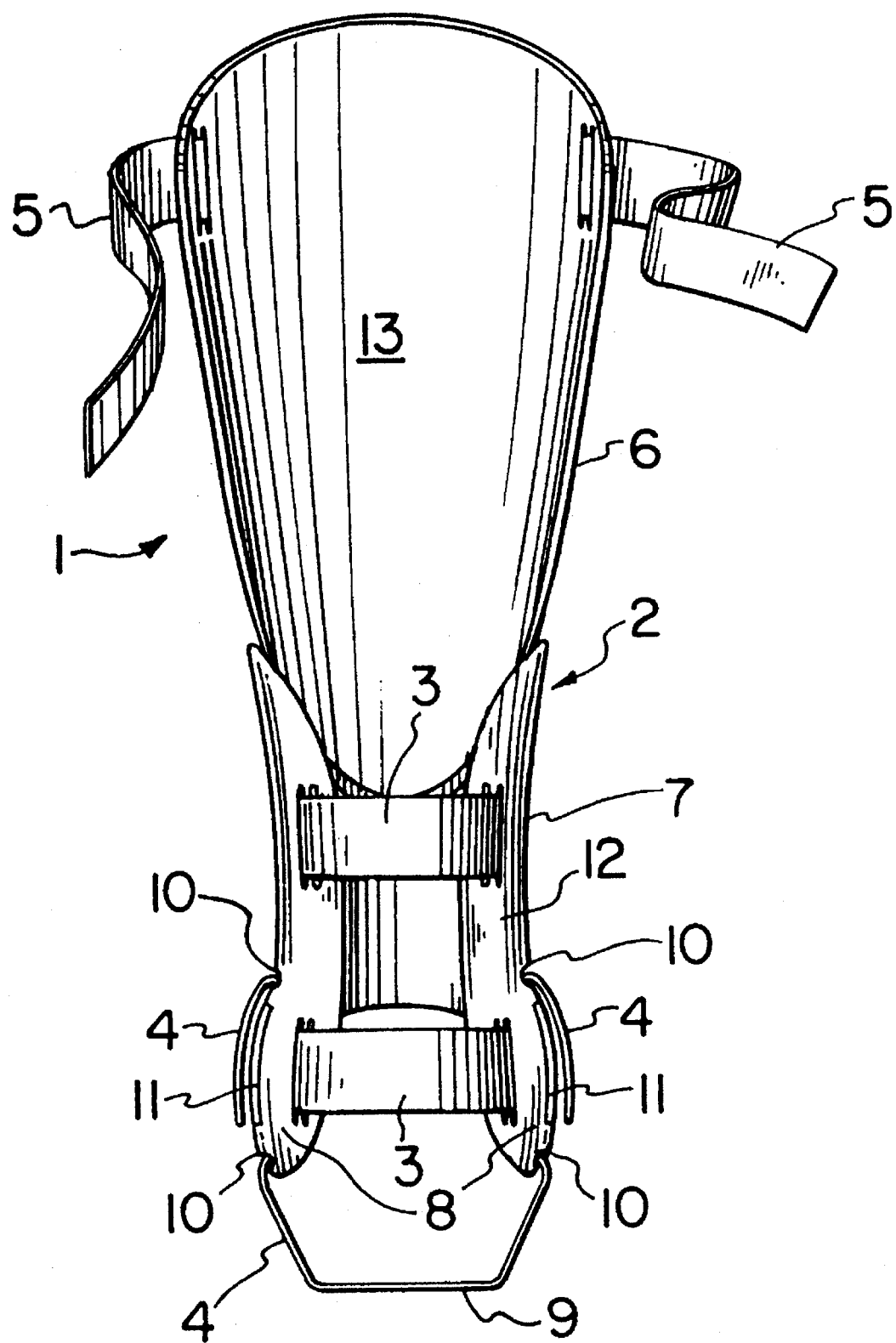
FIG. 3 is a rear elevation view of the first embodiment of the invention.

Referring to FIGS. 1 to 6, a device 1 includes a body 2, securing straps 3, a U-shaped support 4 and a positioning strap 5. The body 2 has a shin protecting portion 6, which is designed to protect the shin from blows, and an ankle supporting portion 7, which is designed both to support the ankle against inversion and eversion and to protect the ankle from blows. Ankle support is effected by placing the two sides 8 of the ankle supporting portion 7 on either side of the ankle, by securing the sides 8 snugly to the ankle with the securing straps 3, and tightening the U-shaped support 4 under the foot. The securing straps 3 are attached to the ankle supporting portion 7 by a known method, such as a hook and loop fastener or a buckle. The U-shaped support 4, which has a wider portion 9, passes through slots 10 in the sides 8 before attaching to the sides 8 by a hook and loop fastener 11. The positioning strap 5 is attached to the shin protecting portion 6 by a known method, such as a hook and loop fastener or a buckle. The securing straps 3, the U-shaped support 4 and the positioning strap 5 are all adjustable in length. The body 2 is made of a single moulded plastic shell 12 and an inner pad 13 (see FIG. 3).

In operation, the body 2 is placed on the lower leg such that the shin protecting portion 6 covers the shin, and the two sides 8 of the ankle supporting portion 7 rest on the lateral and medial sides of the ankle respectively. The securing straps 3 are then passed around the back of the ankle and tightened so that the sides 8 are held firmly on the ankle. The U-shaped support 4 is passed under the foot such that the wider portion 9 rests squarely on the sole of the foot. After passing through slots 10, the U-shaped support 4 is tightened by way of the hook and loop fastener 11. The ankle is thus supported against inversion and eversion, while the dorsiflexion and plantarflexion of the ankle remains substantially unhindered. The shape of the ankle supporting portion 7, and its construction from a plastic shell 12 and inner pad 13, also provides protection to the ankle from blows. Similarly, the shape and structure of the shin protecting portion 6 provides substantial protection from blows. Furthermore, the shape of the device 1 facilitates the wearing of a sock or other article of clothing thereover, and the playing of sports such as soccer or field hockey is substantially unhindered.

Figure 7:
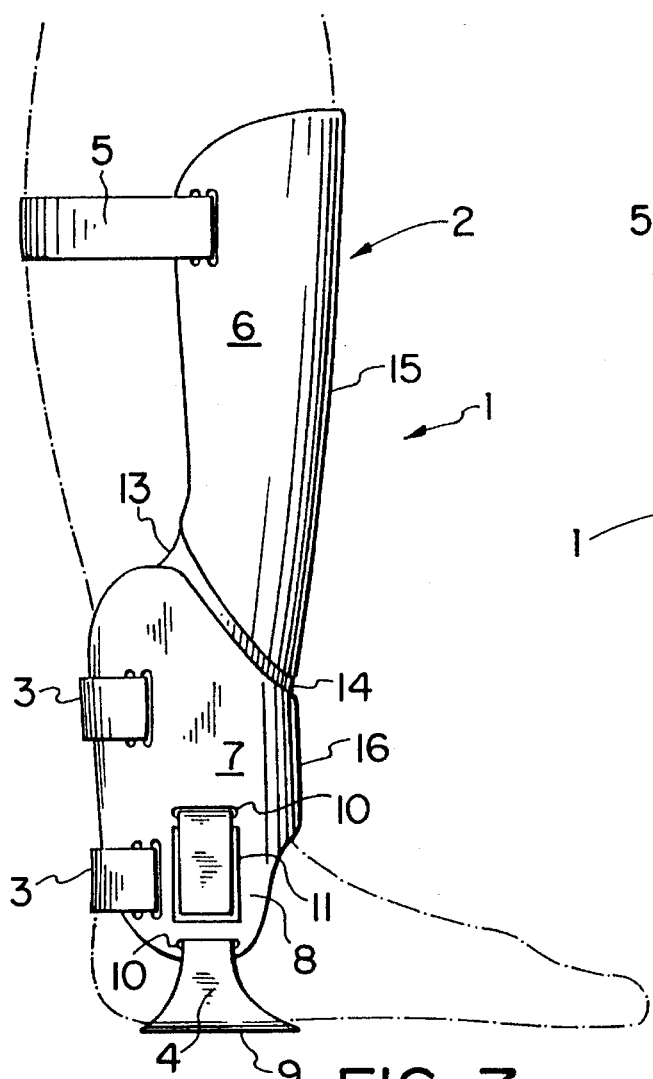
FIG. 7 is a side elevation view of a second embodiment of the invention.
Figure 8:
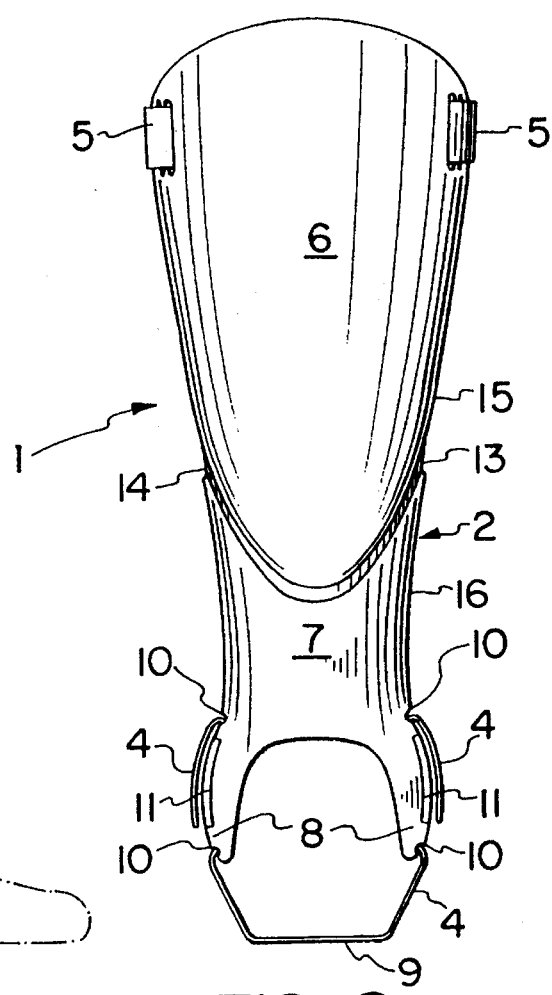
FIG. 8 is a front elevation view of the second embodiment of the invention.

FIGS. 7 and 8 illustrate a further embodiment of the invention, in which the shin protecting portion 6 and the ankle supporting portion 7 are flexibly connected at a flexible connection 14. The flexible connection 14 may be made of various flexible materials, such as cloth, rubber or foam. In the illustrated embodiment, the flexible connection 14 is supplied by the inner pad 13 which spans the gap between the upper shell 15 of the shin protecting portion 6 and the lower shell 16 of the ankle supporting portion 7. Alternatively, the flexible connection 14 could be a separate component.

Figure 9:
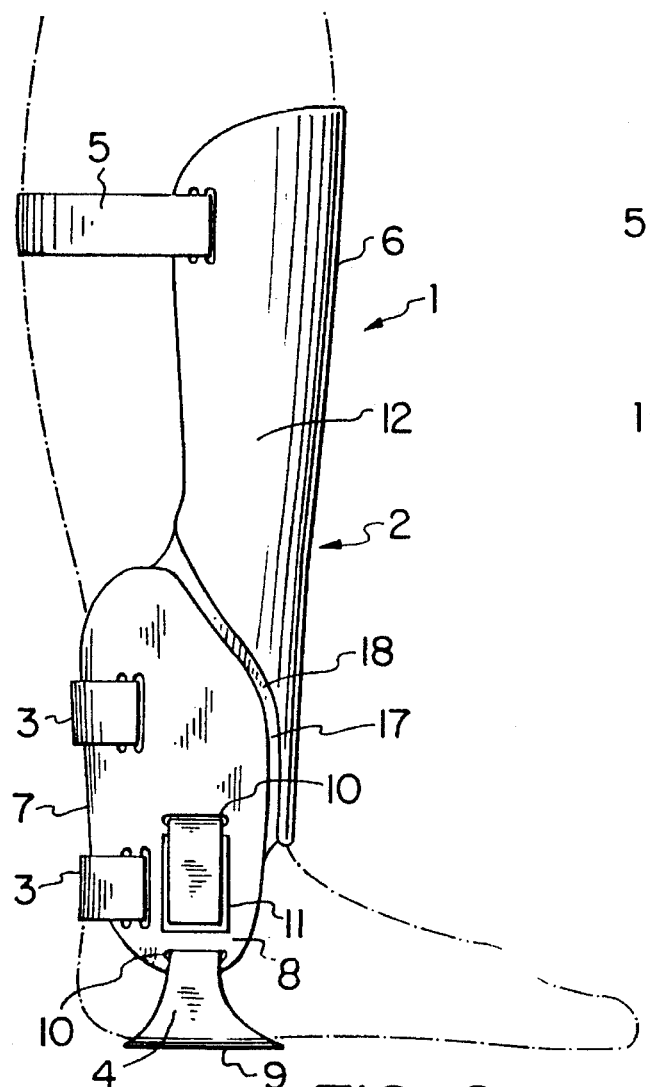
FIG. 9 is a side elevation view of a third embodiment of the invention.
Figure 10:
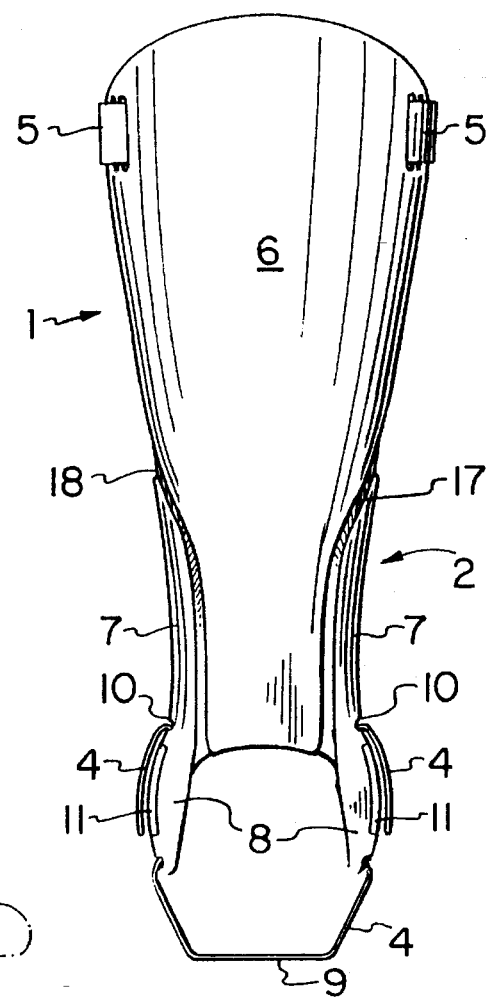
FIG. 10 is a front elevation view of the third embodiment of the invention.

In a third embodiment, shown in FIGS. 9 and 10, the single moulded plastic shell 12 has two flexible zones 17. The zones 17 are made flexible by the perforations 18 in the shell 12. The perforations 18 may be in the form of slits, as in the embodiment of FIGS. 9 and 10, or may be another shape, such as circular.

In a fourth embodiment, shown in FIGS. 11 and 12, the shin protecting portion 6 and the two sides 8 are separate units, flexibly connected only by the securing straps 3 which pass through slots 19 located in both the sides 8 and the shin protecting portion 6. In a similar embodiment, the securing straps 3 would provide the flexible connection 14 between the shin protecting portion 6 and a unitary ankle supporting portion 7, similar to that shown in FIGS. 7 and 8.

The Embodiments of the Invention in Which an Exclusive Property or Privilege is claimed are Defined as Follows:

1. A shin and ankle protective device comprising:

a shin protecting portion for protecting the shin from blows;

an ankle supporting and protecting portion for supporting the ankle against inversion and eversion and for protecting the ankle from blows, the ankle supporting and protecting portion comprising two sides adapted to be positioned on the medial and lateral sides of the ankle respectively, means for tightly securing the two sides of the ankle supporting and protecting portion to the ankle, and a U-shaped support extending between the two sides of the ankle supporting and protecting portion for passing tightly under the foot; and a flexible connecting portion attached to the shin protecting portion and to the ankle supporting and protecting portion for allowing pivoting of the ankle supporting and protecting portion relative to the shin protecting portion during use of the device.

2. A device as defined in claim 1, further comprising a shell extending over the shin protecting portion and the ankle supporting and protecting portion, the shell comprising perforations located between the shin protecting portion and the ankle supporting and protecting portion.

3. A device as defined in claim 1, further comprising a shell extending over the shin protecting portion and the ankle supporting and protecting portion, the shell comprising a thin section located between the shin protecting portion and the ankle supporting and protecting portion.

4. A device as defined in claim 1, the shin protecting portion and the ankle supporting and protecting portion each comprising a shell.

5. A device as defined in claim 4, further comprising an inner pad extending over the shin protecting portion and the ankle supporting and protecting portion, the pad providing the flexible connection between the shin protecting portion and the ankle supporting and protecting portion.

6. A device as defined in claim 1, the shin protecting portion and the two sides of the ankle supporting and protecting portion each comprising a shell.

7. A device as defined in claim 4, further comprising an inner pad extending over the shin protecting portion and the ankle supporting and protecting portion, the pad providing the flexible connection between the shin protecting portion and the ankle supporting and protecting portion.

8. A device as defined in claim 1, the securing means comprising one or more adjustable straps attached to the ankle supporting and protecting portion for extending around the back of the ankle.

9. A device as defined in claim 1, the U-shaped support comprising an adjustable strap with a wider central portion for positioning under the foot.

10. A device as defined in claim 1, further comprising means for maintaining the position of the shin protecting portion on the shin.

11. A device as defined in claim 10, the position maintaining means comprising one or more adjustable straps attached to the shin protecting portion for extending around the calf.

* * * * *

UNITED STATES PATENT AND TRADEMARK OFFICE
CERTIFICATE OF CORRECTION

PATENT NO. : 5,507,720
DATED : April 16, 1996
INVENTOR(S) : George Lampropoulos

It is certified that error appears in the above-identified patent and that said Letters Patent is hereby corrected as shown below:

In the claims, column 4, claim 7, line 29, "4" should read --6--.

Signed and Sealed this

Twenty-seventh Day of August, 1996

Attest:

BRUCE LEHMAN

Attesting Officer  Commissioner of Patents and Trademarks